(12) United States Patent
Burgmeier et al.

(10) Patent No.: US 7,776,078 B2
(45) Date of Patent: Aug. 17, 2010

(54) CATHETER BALLOON WITH IMPROVED RETENTION

(75) Inventors: Robert Burgmeier, Plymouth, MN (US); Richard Goodin, Blaine, MN (US)

(73) Assignee: Boston Scientfic Scimed, Inc., Maple Grove, MN (US)

( * ) Notice: Subject to any disclaimer, the term of this patent is extended or adjusted under 35 U.S.C. 154(b) by 2045 days.

(21) Appl. No.: 10/443,227

(22) Filed: May 22, 2003

(65) Prior Publication Data
US 2004/0236398 A1 Nov. 25, 2004

(51) Int. Cl.
*A61F 2/06* (2006.01)
*A61M 29/00* (2006.01)
(52) U.S. Cl. .................... 623/1.11; 606/194
(58) Field of Classification Search .......... 606/191, 606/194, 195, 198, 108; 623/1.11
See application file for complete search history.

(56) References Cited

U.S. PATENT DOCUMENTS

| | | | |
|---|---|---|---|
| 4,576,850 A | 3/1986 | Martens | 428/156 |
| 4,672,020 A | 6/1987 | Koelsch et al. | 430/166 |
| 4,732,152 A | 3/1988 | Wallsten et al. | 128/343 |
| 4,796,629 A | 1/1989 | Grayzel | 128/344 |
| 4,848,343 A | 7/1989 | Wallsten et al. | 128/343 |
| 4,875,480 A | 10/1989 | Imbert | 128/343 |
| 4,950,227 A | 8/1990 | Savin et al. | 604/8 |
| 5,011,494 A | 4/1991 | Von Recum et al. | 623/11 |
| 5,108,416 A | 4/1992 | Ryan et al. | 606/194 |
| 5,147,763 A | 9/1992 | Kamitakahara | 430/320 |
| 5,389,314 A | 2/1995 | Wang | 264/25 |
| 5,403,341 A | 4/1995 | Solar | 606/198 |
| 5,421,955 A | 6/1995 | Lau et al. | 216/48 |
| 5,458,572 A | 10/1995 | Campbell et al. | 604/96 |
| 5,573,520 A | 11/1996 | Schwartz et al. | 604/282 |
| 5,647,848 A | 7/1997 | Jorgensen | 604/96 |
| 5,662,703 A | 9/1997 | Yurek et al. | 623/1 |
| 5,690,644 A | 11/1997 | Yurek et al. | 606/108 |
| 5,741,429 A | 4/1998 | Donadio, III et al. | 216/8 |
| 5,772,669 A | 6/1998 | Vrba | 606/108 |
| 5,848,987 A | 12/1998 | Baudino et al. | 604/54 |
| 5,855,802 A | 1/1999 | Acciai et al. | 216/8 |
| 5,865,755 A | 2/1999 | Golub | 600/485 |
| 5,902,475 A | 5/1999 | Trozera et al. | 205/655 |

(Continued)

FOREIGN PATENT DOCUMENTS

EP  0 696 447 B1  1/2000

(Continued)

OTHER PUBLICATIONS

U.S. Appl. No. 09/697,608, filed Oct. 26, 2000, Fernando DiCaprio.

*Primary Examiner*—Vy Q Bui
(74) *Attorney, Agent, or Firm*—Vidas, Arrett & Steinkraus, P.A.

(57) ABSTRACT

A catheter for delivering a medical device into a body lumen, and method for preparing said catheter, wherein the catheter comprises an elongate body, at least a portion of which defines a medical device retaining region for retaining a medical device thereon. At least a portion of the medical device retaining region comprises a predetermined pattern of material. The predetermined pattern of material is a photoresist material that may be placed on the outer surface of the catheter to modify at least one physical property of the catheter.

17 Claims, 6 Drawing Sheets

U.S. PATENT DOCUMENTS

| | | | | |
|---|---|---|---|---|
| 6,019,784 A | 2/2000 | Hines | ............................. | 623/1 |
| 6,024,764 A | 2/2000 | Schroeppel | ..................... | 623/1 |
| 6,027,863 A | 2/2000 | Donadio, III | ................ | 430/320 |
| 6,048,350 A | 4/2000 | Vrba | ........................... | 606/108 |
| 6,107,004 A | 8/2000 | Donadio, III | ................ | 430/320 |
| 6,146,814 A | 11/2000 | Millet | ......................... | 430/320 |
| 6,203,732 B1 | 3/2001 | Clubb et al. | ................... | 264/81 |
| 6,258,099 B1 | 7/2001 | Marieiro et al. | .............. | 606/108 |
| 6,391,502 B1 | 5/2002 | Anderson et al. | .............. | 430/22 |
| 6,542,218 B2 | 4/2003 | Anderson et al. | .............. | 355/47 |
| 6,545,748 B1 | 4/2003 | Trozera | ....................... | 355/104 |
| 6,942,680 B2 * | 9/2005 | Grayzel et al. | ............... | 606/194 |
| 2002/0017503 A1 | 2/2002 | Banas et al. | .............. | 219/69.11 |
| 2002/0030796 A1 | 3/2002 | Anderson et al. | .............. | 355/18 |
| 2002/0038767 A1 | 4/2002 | Trozera | ....................... | 205/667 |
| 2002/0123796 A1 | 9/2002 | Majercak et al. | ............ | 623/1.16 |
| 2002/0123797 A1 | 9/2002 | Majercak | .................... | 623/1.16 |
| 2002/0123798 A1 | 9/2002 | Burgermeister | ............ | 623/1.17 |
| 2002/0188310 A1 | 12/2002 | Seward et al. | ................ | 606/185 |
| 2004/0098110 A1 * | 5/2004 | Williams et al. | ............ | 623/1.21 |

FOREIGN PATENT DOCUMENTS

| | | |
|---|---|---|
| WO | 94/15549 A1 | 7/1994 |
| WO | 00/57816 A1 | 10/2000 |

* cited by examiner

CATHETER BALLOON WITH IMPROVED RETENTION

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to delivery an endoprosthesis such as a stent, graft, vena cava filter or other implantable device. Where an implantable device is to be delivered into a body lumen the catheter may include one or more inflatable portions or balloons.

Many procedures make use of a guide catheter positioned within the vascular system of a patient. The guiding catheter assists in transporting a balloon dilation catheter, or other form of treatment catheter, to the portion of the vessel requiring treatment or inspection. The guide catheter is urged through the vasculature of the patient until its distal end is proximate the restriction. The balloon catheter may then be fed through a lumen in the guide catheter.

In delivering a balloon expandable medical device, it is important that the medical device be accurately positioned on the body or working portion of the balloon. Failure to properly position the medical device on the balloon may result in a non-uniform expansion of the medical device.

Unfortunately, the proper positioning of such a medical device on a balloon catheter can be a challenging task because the medical device is typically mounted on an uninflated balloon. In the uninflated state of the balloon, it is difficult to discern where the proximal and distal cones end and where the body portion of the balloon begins.

Numerous devices have been employed to help secure an expandable medical device, such as a stent onto a catheter. Such devices include pull-back sheaths which extend over the entire stent to retain the stent to a portion of the catheter. Some examples of sheaths may be found in U.S. Pat. No. 5,772,669, U.S. Pat. No. 5,868,755, U.S. Pat. No. 4,732,152, U.S. Pat. No. 4,848,343, U.S. Pat. No. 4,875,480, U.S. Pat. No. 5,662,703, U.S. Pat. No. 5,690,644, WO 94/15549 and others. With many retraction systems, it is necessary to move a portion of a manifold or other retraction device a distance at least equal to the length of the retractable sheath to retract the sheath.

Some systems have been developed which avoid the need for retractable sheaths by providing a stent delivery catheter with one or more self-retracting sleeves. Some examples of delivery catheters having sleeves which may be self-retractable are described in: U.S. Pat. No. 4,950,227, U.S. Pat. No. 5,403,341, U.S. Pat. No. 5,108,416, and others.

In U.S. Pat. No. 4,950,227 to Savin et al., an inflation expandable stent delivery system includes a sleeve which overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Still other systems are known which employ a variety of alternative means for retaining a stent on a catheter and/or balloon prior to deliver. For example, the stent delivery system of U.S. patent application Ser. No. 09/697,608 includes stent securement hubs which engage portions of a stent disposed about a catheter, and EP 696,447 describes delivery catheters comprising runners for circumferentially supporting a prosthesis.

Still other systems have been developed which employ surface features on the catheter surface to aid in retaining the stent thereabout. Some examples of systems having unique surface features are described in: WO 00/57816 wherein catheters are described having a textured or roughened surface for retaining a medical device thereon, U.S. Pat. No. 6,258,099 which describes catheter balloons having engagement protrusions, and U.S. Pat. No. 6,048,350 which describes delivery systems employing a combination of securement hubs and balloon segments to aid in retaining a stent there on.

An advantage of providing a stent delivery catheter with surface features that promote stent retention prior to delivery is that the profile of the catheter may be minimized as there may be no need to include additional sheaths, sleeves or other members which would otherwise overlap the stent and increase the profile of the catheter. Another advantage of providing a catheter with stent retaining surface features is that by removing the need for retractable members, the need for relatively bulky or complex retraction systems is likewise removed, thereby providing a delivery system which may be much more simple and safer to use.

Expandable medical devices such as stents have a wide variety of shapes, sizes and configurations. For example, it is known that a stent having a particular strut pattern may have performance characteristics which are significantly different than a stent having a different strut pattern. As a result, it would be desirable to provide individual catheters with varying types of surface feature patterns in order to maximize the effectiveness of the surface pattern in retaining a stent of a particular configuration. Unfortunately, typical manufacturing processes of catheters do not readily lend themselves to individualized production of different catheter types.

Some, catheters and/or balloons are formed of extruded material which is then shaped or molded into a final shape. Providing dozens of different molds for a wide range of surface feature patterns may be cost prohibitive as well as extremely inefficient from a manufacturing perspective. Thus, it would be desirable to provide a method for applying a unique surface feature pattern to catheters, and particularly to balloons which may be cheaply and easily employed on an individual basis.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. Some of the embodiments are directed to catheters, balloon catheters, guide catheters, medical device delivery catheters, etc. In at least one embodiment, the invention is particularly directed to balloons for use with a catheter for the deliver of medical devices such as stents. Numerous types and configurations of such medical devices are known and the term "catheter" as used herein is merely a convenient term used to designate all such devices and their components.

Some embodiments of the invention are directed to catheters having a textured, partially textured or otherwise marked surface which provides the catheter with improved stent retaining characteristics. The texturing or marking facilitates the positioning of an expandable, implantable medical device on the catheter and increases the securement of a stent or other expandable, implantable medical device to the catheter.

In at least one embodiment of the invention a catheter is provided with a pattern of photoresist material which may aid in the retention of a stent. The photoresist material may be comprised of a wide variety of materials, and may provide any texture pattern desired. The texture of the pattern may include raised or indented areas as may be desired.

In at least one embodiment, the external surface of the catheter includes a pattern of photoresist material provided to removably engage a stent or other implantable medical device that may be disposed about the catheter. In at least some embodiments, the pattern of photoresist and/or secondary material is of different composition than that of the underlying material of the catheter tubing.

In at least one embodiment of the invention, photoresist material is deposited on a balloon or catheter is a continuous film. Alternatively, the photoresist material may be a discontinuous coating or deposit.

In at least one embodiment a tubular member, or a portion thereof, is provided with a photoresist material. The photo resist material may be a positive photo resist material, a negative photoresist material or a combination thereof. When the photoresist material is exposed to a particular type of light, the photoresist will react with the material of the tubular member. Where the photoresist is a negative photoresist, the exposed photoresist material will be rendered insoluble, relative to an etchant, by exposure to the light, while unexposed negative photoresist material will remain soluble to a subsequently applied etchant. Where the photoresist is a positive photoresist material, the exposed photoresist is rendered soluble, relative to an etchant, by exposure to the light, while unexposed positive photoresist material will be insoluble relative to the subsequently applied etchant.

In embodiments including a photoresist material, the photoresist material may be provided with a variety of reaction mechanisms. For example some possible reactions for a negative photoresist material include but are not limited to: photo cross-linking that includes dimerization, photo initiated chain growth polymerization, photo condensation polymerization, and photo functional changes etc. If, on the other hand, the photoresist is positive resist material, some possible reactions may include but are not limited to: photo functional changes, and polymer degradation.

In at lease one embodiment, a catheter, or a portion thereof, is provided with a coating of soft and/or tacky material which is sensitive to a particular wavelength of light, and which upon exposure to a particular wavelength of light will react with the material of the catheter. Depending on the type of light sensitive material used, the material may react to exposure to light in a variety of ways. Such light sensitive materials are collectively referred to herein as photoresists. Some embodiments may include photoresist material that is made to react by exposure to ultraviolet (UV) energy, infrared (IR) energy, and/or other forms of energy or light. However, other light sources having a particular range of characteristic wavelengths also be used.

In order to provide the tubular member with a desired pattern of surface features, in some embodiments a mask defining the predetermined pattern is placed over the photoresist and light is shone through the mask onto selected portions of the photoresist. The unique properties of the light and photoresist cause affected areas of the photoresist material and/or the catheter material itself to react in the manner described above. The mask may be provided with any pattern which may be drawn thereon, and as a result the surface of the catheter may be provided with a wide variety of patterns of cross linked and non-cross linked material thereon.

The unique patterns of surface features that may be supplied to a tubular member in accordance with the present invention allows any catheter or balloon to be readily provided with a surface suitable for engaging and/or retaining any type of stent as may be desired.

In some embodiments of the invention, the material of the tubing may be sufficiently thick or include multiple layers such that a portion of the tubing may itself be characterized as a photoresist. As a result, in some embodiments there will be no need to include an additional coating of photoresist material in order to provide the tubing with the surface features desired. In such embodiments the catheter material will be significantly think and/or diverse enough to prevent damage to the catheter or inhibit performance as a result of the photo-cross linking process.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

Figure 1:
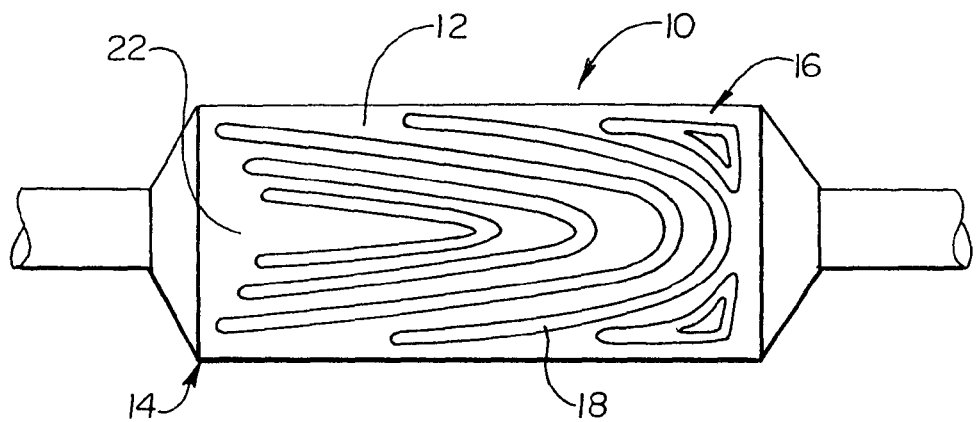
FIG. 1 is a side elevational view of an embodiment of the invention wherein a portion of a catheter is shown with one a pattern of material placed thereon.

The present invention includes many different embodiments. For example, in FIGS. 1 and 2 embodiments of the invention are shown wherein different forms of medical devices, such as a catheter 10 are respectively depicted. As mentioned above, catheter 10 may be any type of elongate medical device or portion thereof, such as a balloon, capable of being inserted into a body lumen and advanced therethrough.

In the various embodiments described herein, catheter 10 may be manufactured from a tubular matrix of material 12. The catheter 10 includes a distal region 14 which has an outer surface 16 having a pattern of indented or raised secondary material 18 thereon. In at least one embodiment the secondary material 18, which comprises the pattern depicted on the catheter surface 16, is a photoresist that has been photo reacted, exposed to an etchant and rinsed in accordance with at least one method such as is described in greater detail below.

Preferably, the secondary material 18 is characterized as being soft or tacky when compared to the surrounding matrix material 12. However, material that is comparatively hard, relative to the matrix material 12 may also be used. In some embodiments of the invention the materials 12 and 18 may be the same or have similar characteristics, but such characteristics may be made different where the material 18 is altered such as by a photo-chemical reaction where one of the materials is a photoresist. For example, where material 18 is a photoresist, and the photoresist 18 is exposed to a particular wavelength of light, the resulting photo-chemical reaction may, for instance, cause a photo cross-linkable photoresist to cross-link at the molecular level thereby potentially altering some of the physical properties of the material 18. Such potential differences between materials 12 and 18 may only be apparent upon reaction of the material 18.

Figure 2:
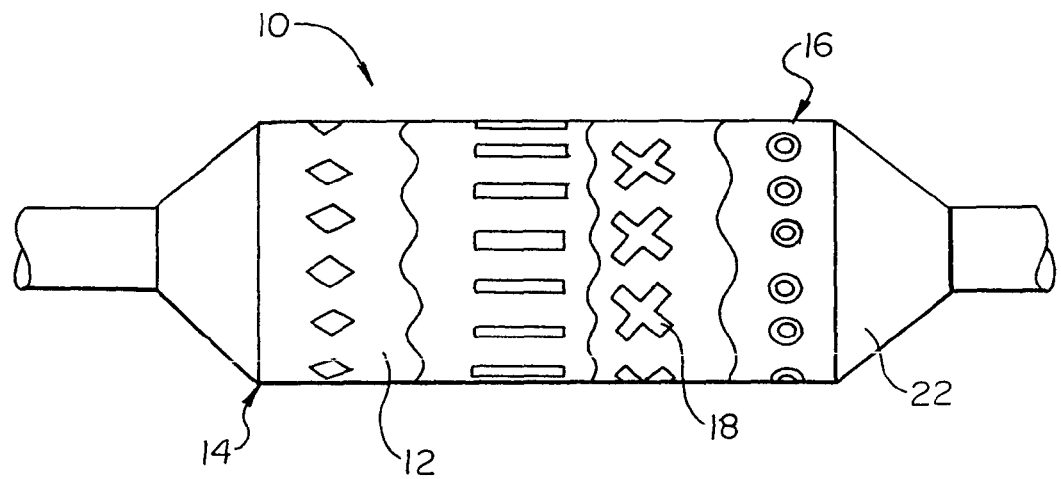
FIG. 2 is a side elevational view of an embodiment of the invention wherein a portion of a catheter is shown with one a pattern of material placed thereon.
Figure 3:
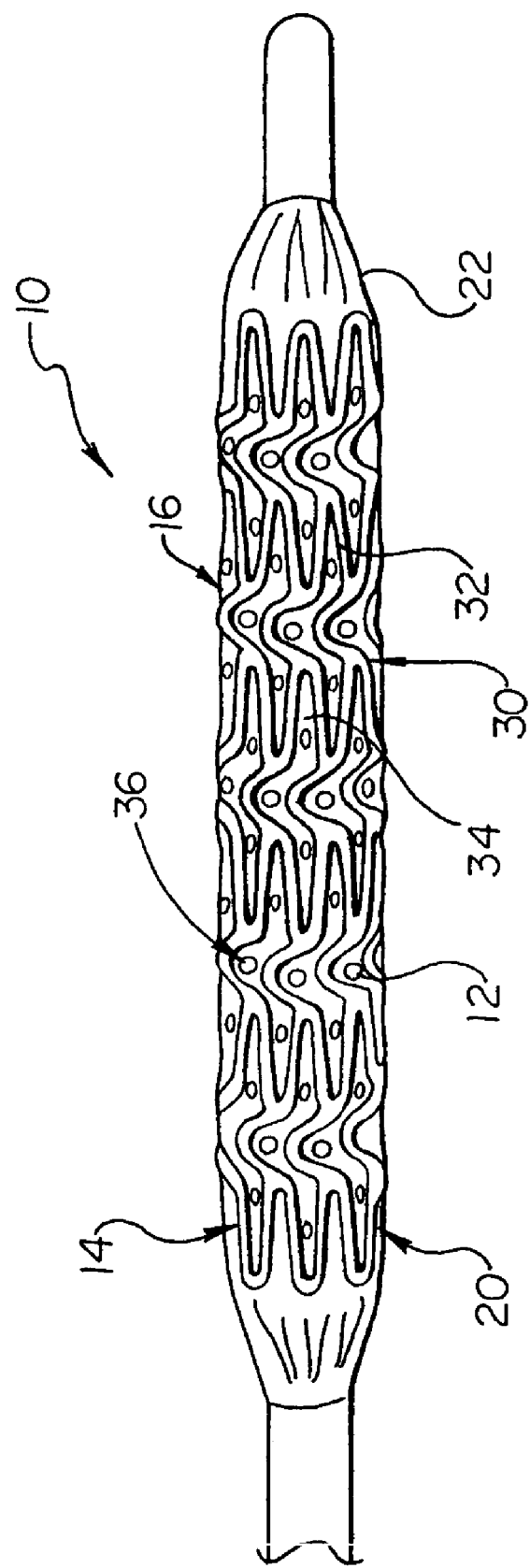
FIG. 3 is a side elevational view of an embodiment of the invention illustrating the engagement of a medical device to a catheter having a pattern of material which corresponds to openings in the framework of the medical device.

FIGS. 1 and 2 illustrate merely two of a near infinite variety of potential patterns of material 18 which a catheter 10 may be configured with. As is shown in FIG. 3, such unique patterns are useful in securing an expandable medical device, such as for example a stent 20 to the catheter surface 16 prior to delivery of the stent 20.

As is known, medical devices such as stents may be self-expandable, balloon expandable or maybe a hybrid of the two more common types. Stents of all types may be included with appropriate embodiments of the present invention. For example, in order to deliver and expand a balloon expandable stent, the distal region 14 of the catheter 10 may be equipped with an expandable member or balloon 22. Where stent 20 is a self-expanding stent or a hybrid device, balloon 22 may be used to trigger or aid in stent delivery and may further be used to seat the stent into place within the body lumen.

In the embodiments shown in FIGS. 1 and 2 the distal region 14 may include a balloon 22 therewith. Where any embodiment of the present invention includes a balloon 22, it is understood that the catheter 10 will further include an inflation means such as an inflation lumen or similar device (not shown) to inflate the balloon 22 for stent delivery or other purposes as is known in the art.

In various embodiments of the invention, the secondary material 18 may be characterized as any substance or substances that alter the physical properties of the catheter 10, particularly the ability of the catheter surface 16 to interact with a medical device such as stent 20 disposed thereabout. For example, where the material 18 is a softer or tackier material than the catheter material 12, the material 18 may provide the catheter 10 with improved ability to removeably engage the stent 20 mounted thereon such as is shown in FIG. 3.

Figure 7:
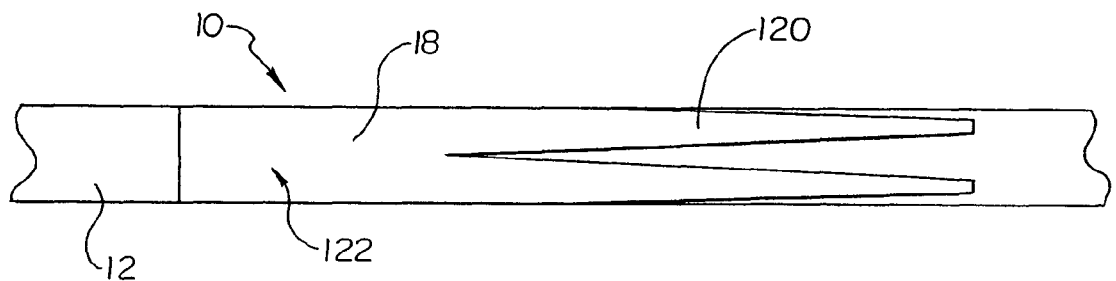
FIG. 7 is a side view of an embodiment of the invention showing a pattern of material placed on a section of catheter tubing.

As is illustrated in FIGS. 1-3, the material 18 may be placed on the external surface of the catheter 10 in any pattern desired. Some additional patterns of material 18 are shown in FIGS. 7-11. In FIG. 7 for example the material 18 comprises a plurality of stripes 120 which increase in thickness as the stripes 120 extend longitudinally along the length of the catheter 10. In some embodiments, the stripes 120 continue to increase until they contact one another to form a continuous band 122 about a portion of the catheter material 12.

Figure 8:
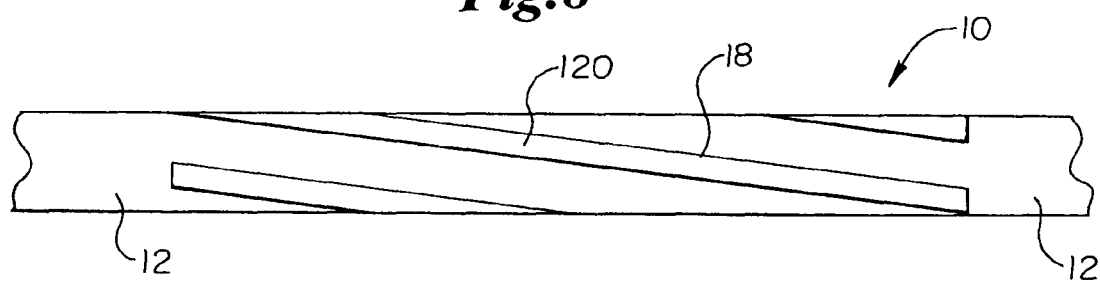
FIG. 8 is a side view of an embodiment of the invention showing a pattern of material placed on a section of catheter tubing.

In FIG. 8 the material 18 is at least one helically oriented strip 120.

Figure 9:
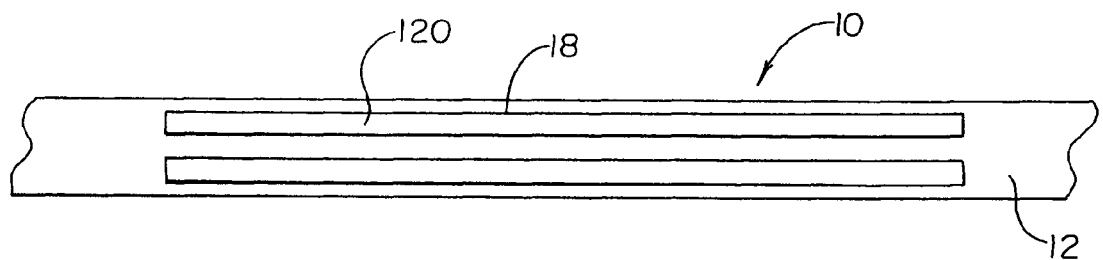
FIG. 9 is a side view of an embodiment of the invention showing a pattern of material placed on a section of catheter tubing.

In FIG. 9 the material 18 is deposited in a pattern of substantially parallel longitudinally oriented stripes 120.

Figure 10:
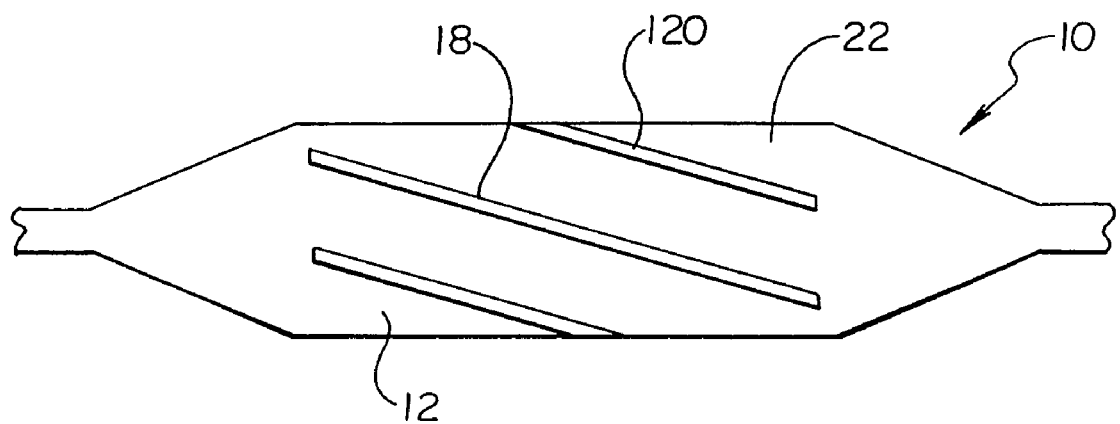
FIG. 10 is a side view of an embodiment of the invention showing a pattern of material placed on a section of catheter tubing.
Figure 11:
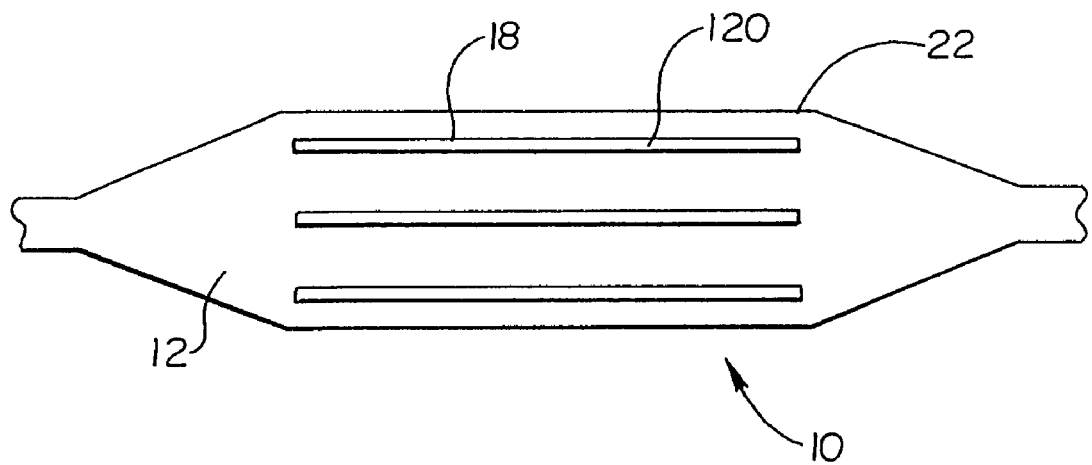
FIG. 11 is a side view of an embodiment of the invention showing a pattern of material placed on a section of catheter tubing.

In FIGS. 10 and 11, the material 18 is shown deposited only on the balloon portion 22 of a catheter 10.

The unique patterns of secondary material 18 used in the various embodiments described herein may provide a catheter or balloon with stiffer or softer segments.

Where material 18 is a photoresist material such as has been described above, photoresist materials may provide a variety of reactions depending on the particular material selected. Several examples of materials and their characteristics are as follows:

A cross-linking reaction may provided for by selective dimerization as seen for cinnamate or a nonselective reaction such as the reaction of a bisazide derived nitrene with an olefin containing polymer.

Cinnamate esters may be made to undergo a 2+2 photo-dimerization to form truxinate or truxillate esters when exposed to the appropriate wavelength of light.

Poly (vinyl cinnamate) may be used as a photoresist and will absorb strongly in the 250-350 nm region.

Other photo-dimerizable groups may be attached to poly (vinyl alcohol) such as napthyl acrylate, styryl acryl ate or furan acrylate however proper sensitizer nitroaromatics (3-nitroacenapthelene) and ketocourmarins (7-propoxy-3-benzoylcoumarin) represent efficient classes of sensitizers.

Polymers that can be photo cross-linked with the reactive groups in the polymer backbone are usually prepared by step growth polymerization, these would include but not be limited to condensation reactions between glycols and diacids, a simple photoactive condensation monomer would be 3,3'-(p-phenyl-ene)bis(ethyl propenate), shown as follows:

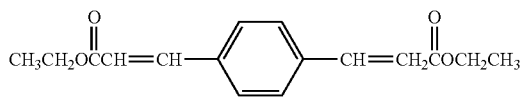

A second positive resist process is chain degradation which increases the solubility of the polymer by cleaving it into smaller pieces, by chain scission, depolymerization, i.e. unzipping or ablation.

Other polymer photo initiated free-radical polymerization typical pairs include dialkoxy acetophenones and benzoin ether which typically undergo scission.

Also benzophenone-Michler's ketones and ketocoumarin-phenoxyacetic acid pairs may be used. Photo initiated cationic polymerization can be done with multi functional epoxides such as Bisphenol_a, diglycidyl ether and vinyl cyclohexane. The exposure of the diaryliodonium or truarylsulfonium salts to light cause these compounds to decompose to several products.

Bisazide-cyclized polyisoprene (CPI) with about 1-5% bisaryl azides compounds is an example of a suitable negative resist.

Cationic Example
(crosslinking)

PAG $\xrightarrow{h\nu}$ H$^+$ + products

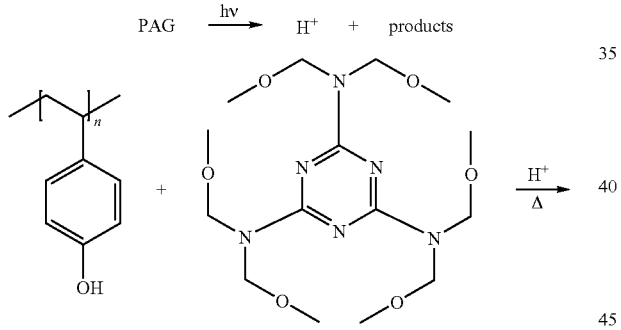

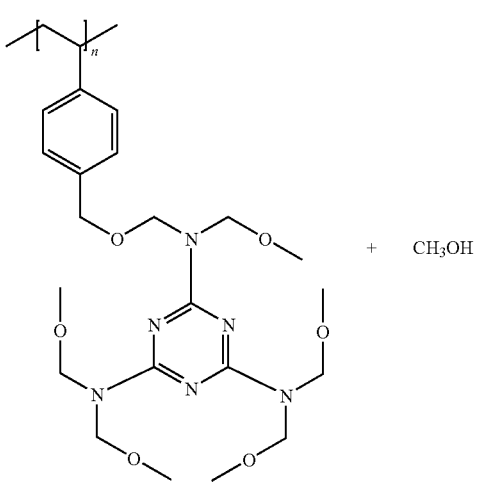

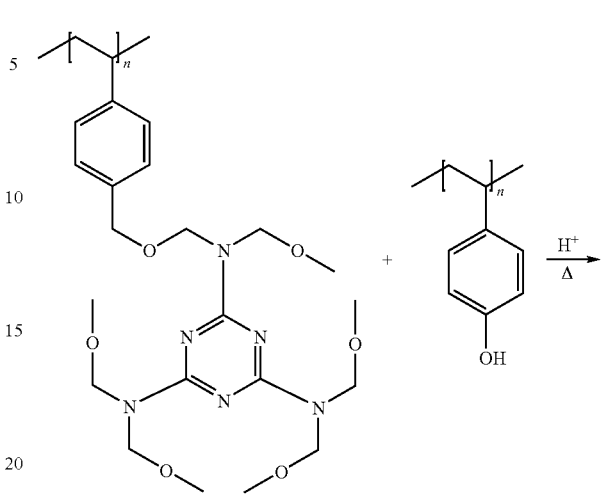

Preferably, photoresist materials 18 are characterized as being soft or tacky when compared to the surrounding material 12. In some embodiments of the invention the materials 12 and 18 may be the same or have similar characteristics, but such characteristics may be made different when the photoresist 18 is exposed to a predetermined type of light energy.

Figure 4:
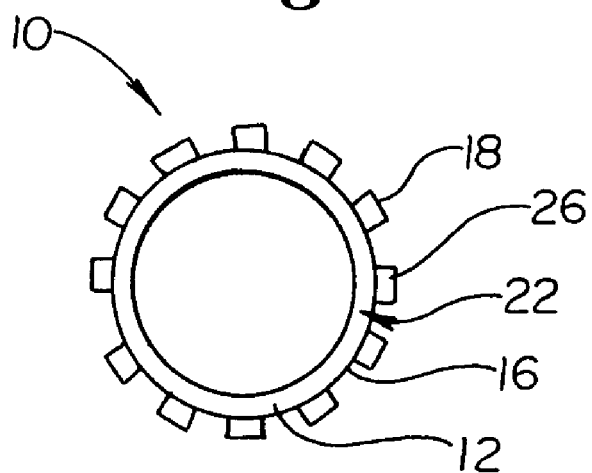
FIG. 4 is a cross-sectional view of an embodiment of the invention.

In the embodiments shown in FIGS. 1 and 2 the unique patterns of photo-reacted material 18 may be raised to extend outward relative to the catheter surface 16. Alternatively the patterns may be depressions or indentations in the catheter surface 16. In FIG. 4, the profile of the catheter 10 may be seen wherein the material 18 extends outward from the surface 16 of the balloon 22. Likewise, in FIG. 5 a catheter 10 having indentations 24 is shown.

Figure 5:
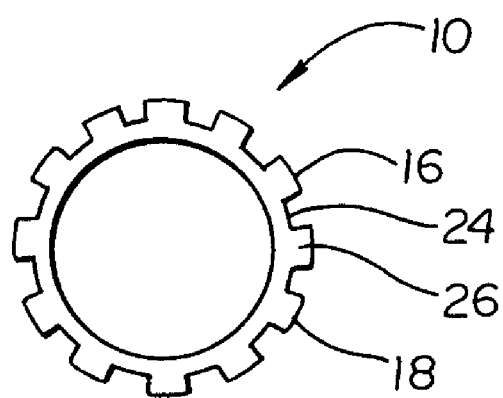
FIG. 5 is a cross-sectional view of an embodiment of the invention.

In the embodiments shown in FIGS. 4 and 5 the pattern of photo-reacted material 18 may be a negative or positive photoresist material 26 which is an inherent part of at least a portion of the catheter surface 16 or may be a coating which is applied to a portion of the catheter surface 16. Using photolithography techniques as described below, selected portions of the photoresist 26 may be rendered insoluble or soluble to an etchant by exposure to a predetermined form of light energy. Where the photoresist 26 is a negative photoresist, portions 18 of the negative photoresist that are exposed to the light energy are rendered insoluble, and the unexposed areas are dissolved or washed away when the photoresist 26 is subsequently exposed to an etchant and then rinsed. Alternatively, where the photoresist 26 is a positive photoresist, portions of the positive photoresist that are exposed to the light energy are rendered soluble to the etchant.

Regardless of the particular pattern of protruding or indented photo-cross linked material 18 provided to the catheter surface 16, the pattern of photo-cross linked material 18 will provide the catheter 10 with a textured surface capable of engaging a stent 20 such as is shown in FIG. 3.

Stents typically comprise a framework 30 of interconnected struts and members 32 which define a plurality of openings 34 therebetween. Stents have a variety of strut patterns as well as a variety of opening sizes and shapes. Catheter 10 may be equipped with a pattern of photo-reacted material 18 which acts to at least partially pass through the various openings of the stent in the reduced configuration. The unique pattern of material 18 may engage the stent 20 to retain the stent in the reduced predelivery state without the need for one or more retaining sheaths or members. Preferably, the individual protrusions 36 of the pattern of material 18 pass at least partially through correspondingly positioned openings 34 of the stent framework 30 to retain the stent 20 to the distal region 14 of the catheter 10 prior to delivery of the stent 20. The protrusions 36 engage the stent 20 by extending into the openings 34 to about 30 percent to about 100 percent of the thickness of the stent 20.

As indicated above, various embodiments of the invention are illustrated in the form of the catheters shown in FIGS. 1-5. These unique devices may be prepared using a photolithography technique which provides for the ability to form or deposit a unique pattern of photo-reacted material 18 on to the surface 16 of a catheter 10. An example of one such technique is depicted, by steps, in FIGS. 6a-6f and is further summarized in FIG. 7.

Figure 6A:
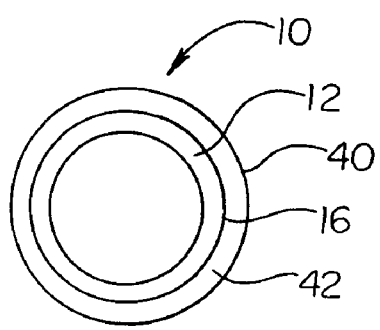
FIGS. 6a-6f are a series of a cross-sectional views illustrating the steps involved in producing a catheter according to an embodiment of the method of the present invention.

In FIG. 6a, a catheter 10 is shown that may be constructed from a wide range of materials and may include on one or more portions of the outer surface 16 of the catheter 10, a layer 40 of soft and/or tacky material 42 which is also characterized as being a photoresist capable of being altered or modified when exposed to light having particular wavelength and intensity characteristics. As indicated above, the photoresist materials may be any photo-reactable material that reacts to some wavelength of light. In the embodiment shown the material 42 is preferably a photoresist that is easily removed from the catheter 10 in a controlled manner. In a more preferred embodiment, the photoresist material 42 is a photo cross-linkable material.

Typically, where the photoresist material 42 is a photo cross-linkable polymer, the process of photo cross-linking is conducted by exposing the photoresist material 42 to light, preferably UV light, of a particular intensity and/or wavelength, for a predetermnined duration depending on the particular material to be cross-linked and the material's thickness. Some additional examples of such photoresist materials 42 include but are not limited to: polydiethynybenzene, novlac, polystyrene, polyvinylphenol, polyimide, and/or CPI-bisazide.

In some embodiments of the invention, particular forms of light may be preferred for use with particular photoresists 42. For example, some light sources may be: vacuum UV 125-200 nm, deep UV 200-300 nm, mid-UV 300-350 nm, near-UV 350-450 nm. In some embodiments, X-ray energy may also be utilized to react with a particular photoresist 42.

As indicated above, some embodiments of the invention include photoresist materials that provide photoinitiated polymerization reaction(s). Such photoinitiated polymerization systems require a suitable chemistry, such that the photoresist may require a polymerizable monomer binder to give the photoresist coating form and flexibility and a developer that dissolves away the unexposed areas while leaving the exposed areas almost unchanged. Binder polymers are usually photographically inert. They are chosen for their flexibility, adhesion and scratch resistance. The photoresist must also contain a photoactive compound (PAC) to initiate the reactions. Some examples of typical PAC materials are the diazoquinones family of compounds, and/or any compound that will undergo an SUS, or Wolft rearrangement reaction, under the proper conditions.

In at least one embodiment the material 42 will utilize a CPI type system. CPI has a preferred degree of tackiness that may be controlled by the degree of cyclization.

Layer 40 may be a coating of photoresist material 42 applied to the catheter surface 16 or may be an inherent part of the catheter or balloon material 12. Where photoresist material 42 is an inherent part of the catheter material 12, the thickness of the catheter material 12 must be sufficient to allow protrusions 36 and/or indentations 24 (respectively shown in FIGS. 4 and 5) to be formed therein without compromising the structural integrity of the catheter 10.

Figure 6B:
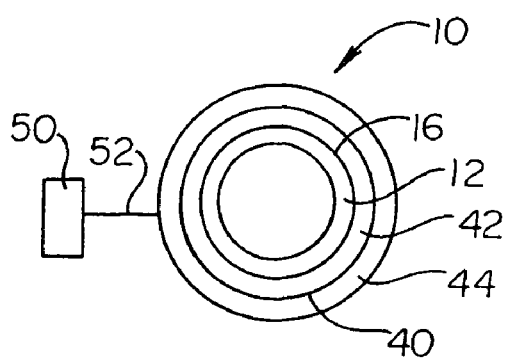

Once the catheter 10 has been prepared, whether by coating with a photoresist material 42 or including the photoresist material in the catheter material 12, the pattern mask 44 may be placed about the catheter 10, such as is shown in FIG. 6b. The pattern mask 44 allows a predetermined wavelength and intensity of light energy, indicated by arrow 52 to pass selectively through portions of the mask 44 to the photoresist material 42 positioned thereunder.

Materials suitable for use in forming mask 44 include but are not limited to: glass, metals, polymers, mylar, or nearly any material desired.

Any pattern which is capable of being drawn or otherwise transferred onto the mask 44 may be utilized. The pattern will typically correspond to the opening pattern of a particular stent but may also be in the form of one or more, regularly or irregularly shaped and/or positioned: hubs, knobs, engagement members, troughs, valleys, channels or other physical elements suitable for providing the catheter with a textured surface 16 such as is shown in FIGS. 1 and 2. More preferably, the textured surface provided to the catheter 10 should provide the catheter 10 with the capacity to retain a stent 20 in the reduced state thereabout prior to delivery, such as is shown in FIG. 3.

Light energy 52 is transmitted from a light energy source 50. An example of a light source 50 is a laser. Light energy 52 photo-chemically reacts with the material 42 in the manner previously described.

The reacted photoresist material 42 may undergo significant changes as exemplified in the diagram immediately below.

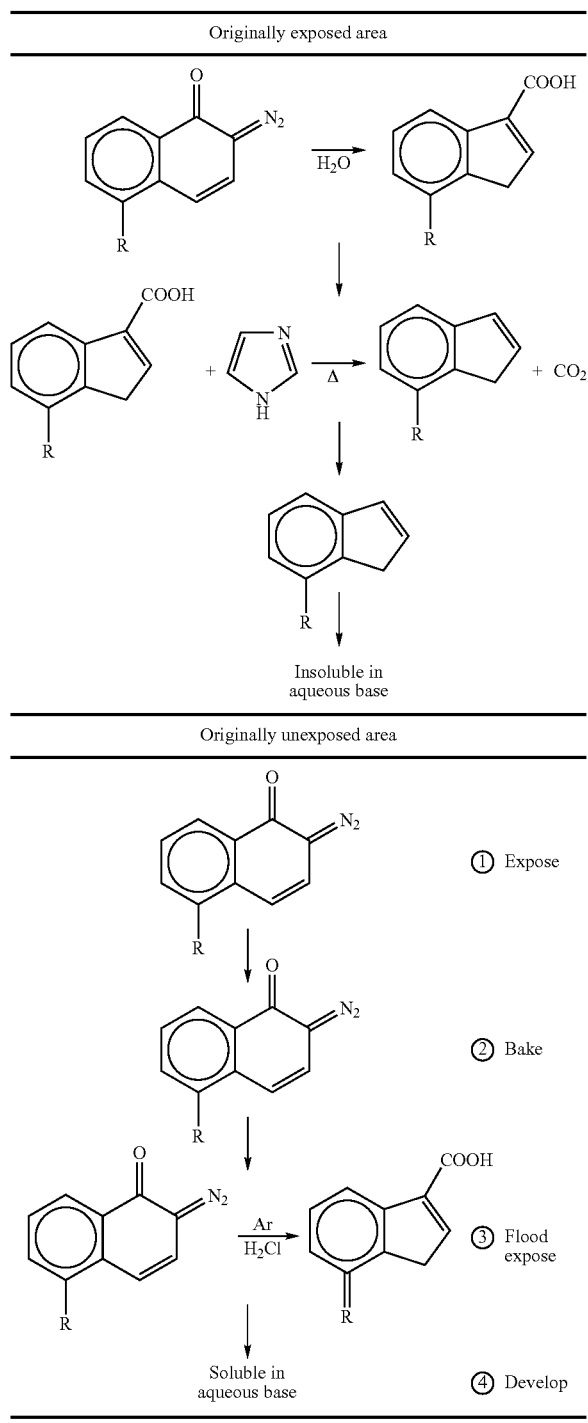

Figure 6C:
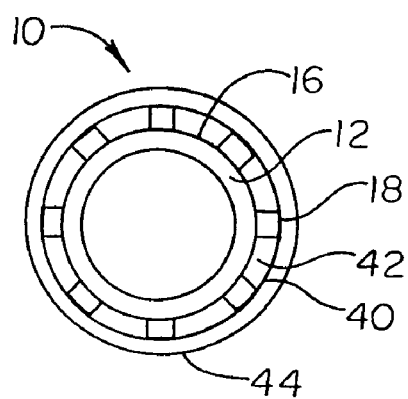
Figure 6D:
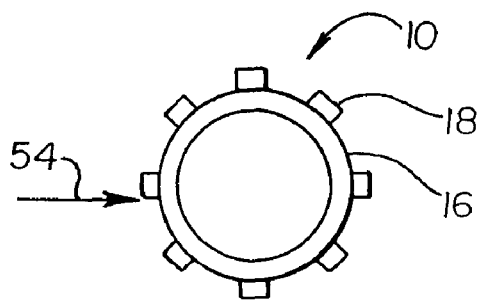

The mask 44 is constructed and arranged to pass light onto the photoresist layer 40 only according to the pattern defined by the mask 44. Where the photoresist layer 40 is a negative photoresist, the areas of the layer 40 that are exposed to light 52 form a cross-linked matrix at the molecular level of the material 42. As is shown in FIG. 6c, the now photo cross-linked, or otherwise photo-reacted, material 18 may be selectively located throughout the layer 42 according to the patter of the mask 44. In the case of a negative photo-resist material, material 18 will remain insoluble to an etchant that is applied to the affected area of the catheter following light exposure, while adjacent areas of the layer 42 are dissolved or rinsed away such as is shown in FIG. 6d.

After the desired photo-reaction, such as cross-linking, has taken place, the mask 44 is removed, and a solvent or etchant, indicated by arrow 54, is applied to the catheter 10. The solvent 54 is constructed and arrange to remove any remaining photoresist material 42 which has, in the case of a positive photoresist: not been exposed to light 54, or in the case of a negative photo resist: has been exposed to the light 54. Some examples of suitable etchants 54 include, but are not limited to: water, hexane, IPA organic and inorganic acids. In addition non-photo-reacted material may be removed by preferential ablation using lasers, plasma and/or ion etching. Plasma etching may utilize Fluorine, Chlorine, $CF_2$, Oxygen, Argon, and/or $CF_4$. Ion etching could use Phosphorus, Boron, Fluorine, and/or Chlorine ions. Laser energy may be supplied by x-mer, YAG, He, etc. In at least one embodiment, following application of the etchant 54, the catheter is rinsed.

Figure 6E:
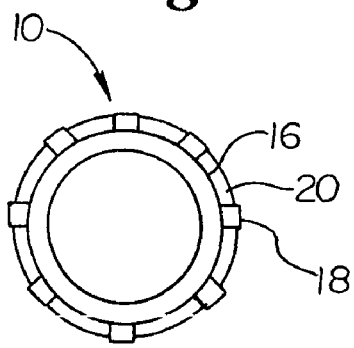
Figure 6F:
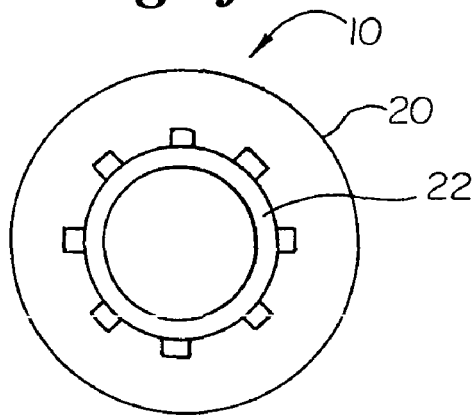

Subsequent to the removal of the excess photoresist material 42, a stent 20 may be mounted on to the catheter 10 by engaging the stent 20 in the reduced state to the pattern of photo cross-linked material 18 such as is shown in FIG. 6e. Where the catheter 10 includes a balloon 22, upon insertion and advancement to a predetermined location with in a body lumen, the stent 20 may be released upon expansion of the balloon 22, as is shown in FIG. 6f.

By employing the unique method depicted in FIGS. 6a-6f, any catheter 10 may be provided with a pattern of surface features suitable for engaging and retaining any type of expandable medical devices, particularly stents, prior to their delivery.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A catheter for delivering a medical device into a body lumen, the catheter comprising:

an elongate body, at least a portion of the elongate body defining a medical device retaining region for retaining a medical device thereon, at least a portion of the medical device retaining region comprising a predetermined pattern of photoresist material, the photoresist material is a positive photo resist material comprising at least one member selected from the group consisting of diazoquinones, phenolic resins, phenolic formaldehyde resins, phenolic resins with about 1-5% bisaryl azide compounds, 3,3'-(p-phenyl-ene)bis(ethyl propionate), dialkoxy acetophenones;

benzoin ethers; benzophenones, Michler's ketones, ketocoumarins-phenoxyacetic acid pairs, multifunctional epoxides, diaryliodonium salts, triarylsulfonium salts, bisazide-cyclized polyisoprene, poly(p-diethynylbenzene), polystyrene; polyvinylphenol; polyimide and combinations thereof.

2. The catheter of claim 1 wherein the predetermined pattern of photoresist material is constructed and arranged to retain the medical device to the medical device receiving region prior to delivery of the medical device.

3. The catheter of claim 1 wherein the medical device retaining region is an expandable balloon.

4. The catheter of claim 1 wherein the predetermined pattern of photoresist material defines at least one raised portion of the medical device receiving region.

5. The catheter of claim 4 wherein the at least one raised portion of the medical device receiving region extends outward from the elongate body.

6. The catheter of claim 5 wherein the medical device is a stent releasably engaged to the at least a portion of the medical device retaining region, the at least one raised portion releasably engaging the stent.

7. The catheter of claim 6 wherein the stent comprises an expandable framework having a plurality of openings therethrough, the at least one raised portion at least partially extending through at least one of the openings in the stent framework to releasably engage the stent framework.

8. The catheter of claim 7 wherein the stent has a reduced state and is expandable to an expanded state, in the reduced state the stent being engaged to the at least one raised portion of the at least a portion of the medical device retaining region, the stent being released from the at least one raised portion when the stent is in the expanded state.

9. The catheter of claim 8 wherein the at least a portion of the medical device retaining region is an expandable balloon.

10. The catheter of claim 1 wherein the predetermined pattern of photoresist material defines at least one indented portion of the medical device receiving region.

11. The catheter of claim 1 wherein the elongate body is constructed from the same material as said predetermined pattern.

12. The catheter of claim 1 wherein the elongate body is constructed from a catheter material, the catheter material and the photoresist material being different materials.

13. The catheter of claim 1 wherein the photoresist material is a photo cross-linkable material.

14. The catheter of claim 1 wherein the photoresist material is a photo cross-linked material.

15. The catheter of claim 1 wherein the photoresist material is a multifunctional epoxide selected from at least one material of the group consisting of bisphenol A, diglycidyl ether, and vinyl cyclohexane, and any combination thereof.

16. The catheter of claim 11 wherein the predetermined pattern of photoresist material is deposited on the catheter material by at least one deposition process from the group consisting of ink jet printing, electrostatic spray, pressurized jet coating, contact printing and any combination thereof.

17. The catheter of claim 12 wherein the predetermined pattern of photoresist material is deposited on the catheter material by at least one deposition process from the group consisting of ink jet printing, electrostatic spray, pressurized jet coating, contact printing and any combination thereof.

* * * * *